United States Patent [19]

Scharf

[11] Patent Number: 4,598,157

[45] Date of Patent: Jul. 1, 1986

[54] METHOD FOR THE MANUFACTURE OF PYROMELLITIC ACID DIANHYDRIDE

[75] Inventor: Helmut Scharf, Schermbeck, Fed. Rep. of Germany

[73] Assignee: Chemische Werke Huls Aktiengesellschaft, Marl, Fed. Rep. of Germany

[21] Appl. No.: 716,924

[22] Filed: Mar. 28, 1985

[30] Foreign Application Priority Data

Jun. 8, 1984 [DE] Fed. Rep. of Germany ....... 3421301

[51] Int. Cl.$^4$ .......................................... C07D 307/91
[52] U.S. Cl. ................................................... 549/239
[58] Field of Search ........................................ 549/239

[56] References Cited

U.S. PATENT DOCUMENTS 4,119,645 10/1978 Auroy et al. .................. 549/250 X
4,252,772 2/1981 Way ................................ 549/250 X
4,435,581 3/1984 Miserlis ......................... 549/250 X

*Primary Examiner*—Richard L. Raymond
*Attorney, Agent, or Firm*—Oblon, Fisher, Spivak, McClelland & Maier

[57] ABSTRACT

A method of separating pyromellitic acid dianhydride from the reaction gas obtained from the gas phase oxidation of 1,2,4,5-tetraalkylbenzene with an oxygen bearing gas in a closed gas circulatory system, comprising, (a) desublimating pyromellitic acid dianhydride by contacting the product gas obtained from said gas phase oxidation reaction with a cold, oxygen bearing gas, (b) catalytically burning the byproducts in the waste gas obtained from the desublimation step, and (c) recirculating a proportionate amount of the byproduct free waste gas to the oxidation reactor for the gas phase oxidation reaction.

8 Claims, 3 Drawing Figures

METHOD FOR THE MANUFACTURE OF PYROMELLITIC ACID DIANHYDRIDE

BACKGROUND OF THE INVENTION

1. Field of the Invention:

The present invention relates to a method of preparing pyromellitic acid dianhydride.

2. Description of the Prior Art:

The manufacture of pyromellitic acid dianhydride (PDMA) is conducted on a large scale by two different methods. One method is a liquid phase oxidation in which 1,2,4,5 tetraalkylbenzene or 2,4,5 trialkylbenzaldehyde reacts with nitric acid or a gas containing oxygen in the presence of a halogen-containing metal catalyst. This reaction does not yield the desired dianhydride, but the free acid, which must be dehydrated in a subsequent step to form the dianhydride. The dehydration step and substantial problems of corrosion make this method expensive and not very attractive.

The second method is a gas phase oxidation in which 1,2,4,5 tetraalkylbenzene, together with air in the gas phase is passed over a heterogeneous catalyst and the dianhydride desublimates when the reaction gas is cooled. In an improvement of the process as described in DE-PS No. 23 62 659, the reaction gas, after initially cooled to a temperature still above the condensation temperature of the PMDA, is further reduced in temperature over cooled surfaces controlled by thermostats to desublimate the PMDA. The temperature of the cooling surfaces must be below the condensation temperature of PMDA, but above the condensation temperature of byproducts of the reaction.

The disadvantage of this and similar methods, which use cooled surfaces to desublimate the PMDA, is that large cooling surfaces are necessary.

Another way in which PMDA can be desublimated from the reaction gas is to additionally cool the reaction gas by direct contact of said gas with a cold gas. Thus, for example, as shown in French Pat. No. A 2 082 822, cold air is added to the reaction gas in two successively arranged tubes. Except for an improvement of the product purity from 95% (without contact of the reaction gas with cold air) to 97% (with contact of the reaction gas with cold air where the ratio of reaction gas to air is 1:1), this process provides no improvement in the conditions of the process. In this disclosed method the wall area of the tubes is additionally a site for desublimation since it serves to conduct heat away from the product. Moreover, the surface of the wall, because it is not actively cooled is much too large for an industrial installation. Thus, for example, in a system having a throughput of 1 t of durene/hr., the wall area amounts to approximately 125,000 square meters. Upon introduction of cold air into the reactor, the method of French Pat. No. A 2,082,822 improves the separation of PMDA from the reaction gases upon its deposition on the reactor wall. This system also has the disadvantage, however, that the apparatus more rapidly clogs during the reaction than normally is the case. Because, as a rule, this method requires a significantly larger, usually doubled quantity of waste gas to be cleansed in comparison to the previously described method, the problem of eliminating the byproducts from the waste gas is compounded. In addition to these disadvantages is the fact that for the total process a double quantity of air, one part for the reaction, and one part for the desublimation, is used, which makes the method more expensive. For all of these reasons, this method has never been utilized in industry.

The problem of fractional desublimation of a material from a reaction gas is not only a problem with PMDA, but also is a problem which is encountered in the manufacture of some other materials. Thus, for example, British Pat. No. 1,081,579 describes a method and an apparatus for the fractional desublimation of terephthalic acid. In this method the reaction product is obtained through the direct cooling of a gaseous material under desublimation conditions, wherein the temperature of the gaseous material must reside below the condensation temperature of the product to be separated, but above the condensation temperature of the byproducts produced in the reaction. In the process the wall surface of the desublimator is adjusted to a temperature above the selected condensation temperature. In order to cool the reaction gas, water in its liquid form is injected into the gas as the preferred cooling agent. This cooling technique however, is not possible in the desublimation of PMDA, because in addition to the PMDA, byproducts would also condense on the water droplets before they completely evaporated. This problem is further compounded by the problem that with the large quantities of water or steam required at the temperatures of PMDA desublimation, the PMDA would be hydrolyzed to the acid. If the water were replaced with a cooling gas, then, when one calculates the gas needed to achieve the same cooling effect of quantities of water, very large quantities of cooling gas would be required, because a portion of the cooling gas would be heated by the walls as a result of the long period of time, 40 sec., that it remains in the condensation zone and therefore would no longer be capable of cooling the reaction gas. These long delay periods of the gas mixture in the condensation zone, in an attempt to transfer this method to the manufacture of PMDA, would also result in apparatus dimensions that would not be managable in industry, and the very large quantities of waste gas would render any sensible cleansing of the waste gas impossible. This method therefore cannot be employed in the manufacture of PMDA.

A need therefore continues to exist for an improved method of isolating pyromellitic acid dianhydride from the gases discharged from the oxidation of tetraalkylbenzene compounds.

SUMMARY OF THE INVENTION

Accordingly, one object of the present invention is to provide a method for manufacturing PMDA by gas phase oxidation in which the three successive steps of oxidizing the starting material to PMDA, the desublimation of PMDA and waste gas processing are so arranged and interconnected that the quantity of gas required per unit quantity of PMDA is the same or only insignificantly larger than the quantity of gas necessary for the oxidation of the educt.

Briefly, this object and other objects of the present invention as hereinafter will become more readily apparent can be attained in a process for manufacturing PMDA in a closed gas loop system by catalytically oxidizing 1,2,4,5-tetraalkylbenzene in an oxygen bearing gas and then isolating PMDA by (a) desublimating pyromelitic acid dianhydride by contacting the product gas obtained from the reaction with a cold, oxygen-bearing gas, (b) catalytically burning the byproducts in the waste gas obtained from the desublimation step, and (c) recirculating a proportionate amount of the byproduct free waste gas to the oxidation reactor for the gas phase oxidation reaction.

BRIEF DESCRIPTION OF THE DRAWINGS

A more complete appreciation of the invention and of the attendant advantages thereof will readily be obtained as the same becomes better understood by reference to the following detailed description when considered in connection with the accompanying drawings, wherein.

DETAILED DESCRIPTION OF THE PREFERRED EMBODIMENTS

In the present invention the desublimation of the PMDA takes place with the aid of a cold gas, the byproducts present in the waste gas after desublimation of PMDA are catalytically combusted and a portion of the waste gas from the catalytic combustion of the byproducts is led back to the main reactor for the production of PMDA, so that a closed gas loop is formed. The remaining portion of the waste gas obtained upon combustion of the byproducts is released into the atmosphere and/or is led back to the desublimation stage, thereby forming a second closed gas loop.

The method of the present invention has the advantage that the desublimation of the PMDA can be performed directly with a cooling gas without augmenting the total amount of gas per unit quantity of PMDA for the total process. This makes the overall process simpler and more reliable. Although the process uses a cooling gas for desublimation, it is not as inexpensive. Because a portion of the waste gas obtained from the catalytic combustion of the byproducts of the process can be returned to the desublimation step, the gas requirement for the total system can be reduced even more than usually is the case. A further advantage of the method is that the waste gas obtained from the catalytic combustion of byproducts is so clean that it can be released directly into the atmosphere, thereby obviating the requirement for a high smokestack. Simultaneously, this method significantly simplifies the processing of the waste gas out of the desublimation, both with respect to apparatus and methodology, it eliminantes the need for byproduct removal and it provides additional energy for the reaction system by utilizing the heat of combustion obtained from the byproducts, so that the method provides a number of economic and ecological advantages relative to the prior art.

Figure 1:
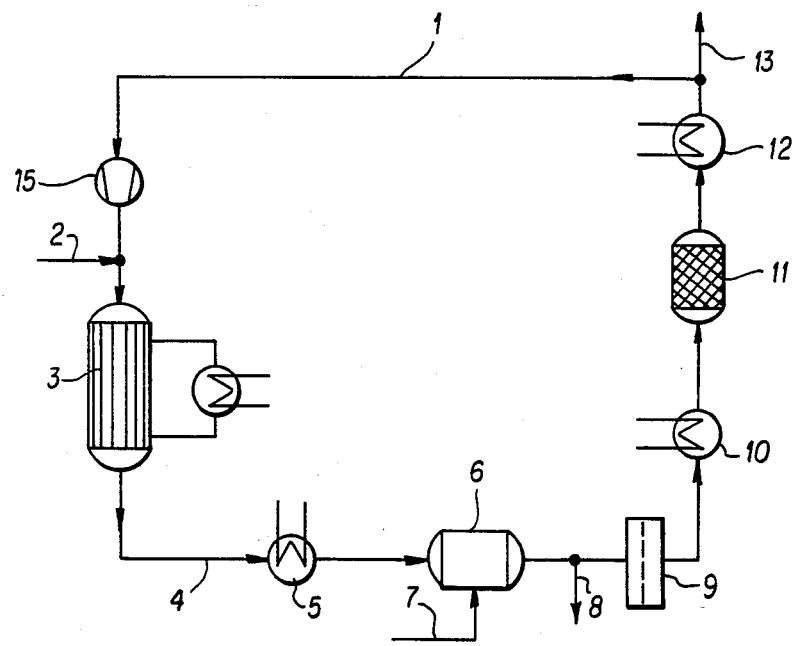
FIG. 1 shows the closed circulatory system of the present invention in which pyromellitic acid dianhydride is synthesized and desublimated.
Figure 2:
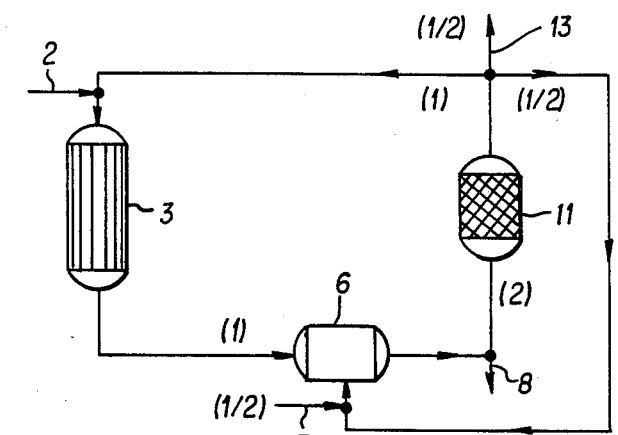
FIG. 2 is an embodiment of the system shown in FIG. 1 which contains a second closed gas loop.
Figure 3:
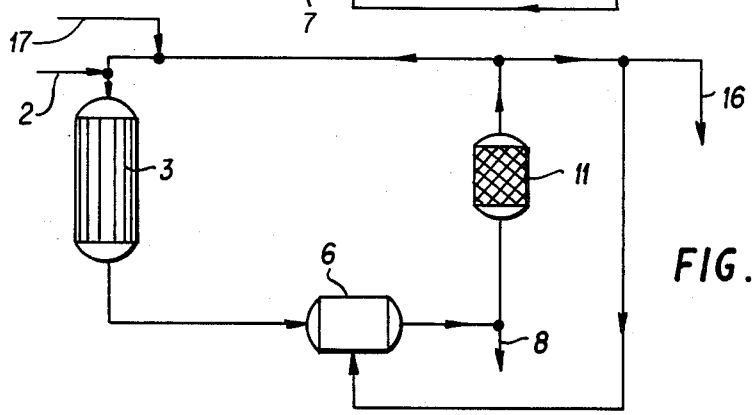
FIG. 3 is an embodiment of the system shown in FIG. 1 which shows another form of a second closed gas loop.

Reference is now made to FIGS. 1-3 for a further understanding of the process of the invention.

In FIG. 1, hot air originating from the circulatory process is led into the reactor (3) through the line (1). Before it reaches the reactor, tetraalkylbenzene is injected into the hot air stream through line (2). The temperature of the air can vary over a very wide range, but it should lie above the condensation point of the starting material in air. The tetraalkylbenzene can be injected into the air flow in liquid form, or it can be conveyed in a gaseous state and then mixed with the hot air. The ratio of starting material to air depends on the catalyst employed and on the desired temperature and flow conditions in the catalyst bed. As a rule, the weight ratio will reside within the range of approximately 0.01 to 0.25:1.

The substituents in the 1,2,4,5 positions of the benzene nucleus of the starting material are not limited to alkyl groups, but may include other substituents as well, as long as they include a carbon atom immediately adjacent the benzene ring and form carboxylic acid anhydrides under the reaction conditions. Because of the number of possible compounds, each individual case must be examined to determine whether a given compound is suitable for the method. In the present method, the air can be replaced by oxygen that has been thinned with other inert gases, such as carbon dioxide, water, steam, and the like that do not interfere with the oxidation reaction, the desublimation step and the catalytic combustion of the waste gases. If other gases are used in place of nitrogen to thin the oxygen, it must be determined in each instance whether the gas does not disrupt the circulatory process in the subsequent steps. Air is particularly preferred as the circulatory gas.

After the oxidation of the tetraalkylbenzene in the reactor (3), the reaction gas, which contains PMDA and a number of other byproducts, passes through the line 4 into the heat exchanger (5) where it is cooled to a temperature slightly above the condensation point of the PMDA in the reaction gas. The condensation point itself is dependent on the concentration of PMDA in the reaction gas, which, in turn, depends on the proportion of tetraalkylbenzene in the air in front of reactor (3) and on the reaction conditions in the reactor (3).

The precooled reaction gas gas is then cooled in the desublimator (6), by mixing with a cold gas (7), down to a temperature which is below the condensation point of the PMDA and yet above the condensation point of the byproducts. The temperature at which the desublimation is to occur depends on the concentration of PMDA in the reaction gas, the type of cooling gas used, the desired degree of separation for PMDA and the type and quantity of byproducts in the reaction gas. Gases which qualify as coolants for the reaction gases are those which do not react with the PMDA under the desublimation conditions and which do not disrupt the subsequent catalytic post-combustion and the oxidation of the PMDA raw material. Gases are preferred that contain oxygen, because this makes it possible to introduce the oxygen into the circulatory process that is necessary for the manufacture of the PMDA. Suitable gases include oxygen and nitrogen and/or carbon dioxide and/or water (steam). Air is particularly preferred as the cooling gas. It can also be advantageous to use oxygen-bearing waste gases from other production systems, if they contain materials which can be burned in the catalytic post-combustion and do not disrupt the desublimation, such as, for example, carbon monoxide and hydrocarbons, which boil easily. Simultaneously, the use of these waste gases reduces the waste problem of the corresponding production system.

The quantity of cooling gas required depends on the desired desublimation temperature and the temperature of the cooling gas. The quantity should be kept as small as possible in order not to have to move large quantities of gas. Of course, the temperature of the cooling gas must lie below the selected desublimation temperature. Because smaller quantities of gas are required, the lower the temperature of the cooling gas is, gases with low temperatures are preferred. Gases at room temperature are particularly suitable. However, gases at temperatures below room temperature can also be employed, but because these gases must first be cooled before they can be employed, and cooling energy is expensive, as a rule it does not make sense to cool the gases to a temperature below room temperature. When cooling gases are employed at room temperature, the ratio of cooling gas to reaction gas, which depends on the PMDA content in the reaction gas, the desired degree of separation for PMDA and the required purity of the PMDA, generally is about 0.4–1.5:1 and is particularly preferred at about 1:1.

The PMDA which desublimates in the desublimator (6) is separated from the gas with the aid of filter (9) and is drained off through line (8). The gas, which still contains all byproducts, is brought to a temperature in the heat exchanger (10) which is sufficient to begin the catalytic and adiabatic combustion of the byproducts in the reactor (11). The waste gas from the catalytic post-combustion contains, in addition to the gas components of the cooling gas for the desublimation, carbon dioxide and water (steam) from the main reaction in reactor (3) and the post-combustion of the byproducts in reactor (11).

As a rule, the waste gas from reactor (11) is so clean that after the heat of combustion from the byproducts is recovered in the heat exchanger (12), a portion of the gas is released through line (13) into the atmosphere, while the remaining portion of gas is led through line (1) back to compressor (15) and reactor (3), so that a closed gas loop is formed. The volume distribution between the two gas courses (13) and (1) is adjusted according to the ratio of reaction gas to cooling gas in the desublimator (6). For the particularly preferred ratio of about 1:1, the split ratio of the two gas courses (13) and (1) is also about 1:1. Instead of cooling the entire quantity of waste gas from the catalytic post-combustion, it is also possible to cool only the waste gas which is drained off and to lead the circulating gas through line (1) into reactor (3) at the temperature at which it emerges from post-combustion reactor (11).

With the aid of the gas circulation system of the present invention, it is possible to perform the desublimation of the PMDA with a cooling gas without increasing the overall gas consumption of the process. While the previously employed methods of the prior art admix the air in front of the reactor exclusively for the oxidation of the alkylaromatic starting material, in the method of the present invention, the oxygen-bearing gas, which is first introduced into the process in the desublimation stage, has a double function. It serves first as a cooling gas for the desublimation, and, secondly, it provides the oxygen for the main oxidation reaction (PMDA production) and the catalytic combustion of the waste gas (combustion of the byproduct). In the conventional method the reaction gas obtained from the desublimation of the PMDA is subjected to the cooled surfaces of an expensive waste gas scrubber of unsatisfactory effectiveness and is subsequently released into the air. The method of the present invention, on the other hand, subjects the waste gas from the known desublimation method to a cooling gas from a known catalytic post-combustion. In the present invention, the gas obtained from the catalytic post-combustion is divided. One portion is led back to the reactor for the production of PMDA, while the other portion is released into the atmosphere. The built up quantities of carbon dioxide and water produced in the two reactors used in this method are released to the atmosphere together with this latter portion of the waste gas. By returning a portion of the waste gas into the main reactor it is possible, according to the method of the invention, to give the cooling gas employed for the desublimation the desired double function of being both the cooling gas and the oxygen bearer, so that despite the desublimation of the PMDA with a cooling gas, no more gas is required in this method than in the previously used methods.

In addition to the above-described and preferred circulatory process, there are other variations of this method that lie within the framework of the invention. For example, in the process shown in a very simplified scheme in FIG. 2, a portion of the waste gas from the catalytic post-combustion of waste gas can be returned to the desublimation device (6) after cooling, so that two closed loops are formed that run together in the area of the desublimation and post-combustion chambers. One possible distribution of the gas flow is also shown in FIG. 2. The returned circulatory gas for the desublimation step is efficiently mixed with cold air. However, in principal, the air can also be introduced at another location in the two circulatory loops, for example, in front of the reactor. In this case the returned waste gas flow must be correspondingly larger. The return of a portion of the waste gas into the desublimation stage has the advantage that, overall, less air is required, but also the disadvantage that the partial pressure of the oxygen in the circulatory gas for the production of the PMDA is somewhat lower than in the preferred method.

In a further variation of the method of the present invention as shown in FIG. 3, nitrogen and/or carbon dioxide are used as the circulatory gas in both loops, the gas loop for the main reaction and the gas loop for the desublimation. The carbon dioxide and water (FIG. 3, line 16) produced during the main reaction and the post-combustion of the byproducts are removed from the gas loop for the desublimation step with the aid of methods known in the prior art. The oxygen required for the two reactions (FIG. 3, line 17) is supplied in pure form, most effectively in front of the reactor, for the production of the PMDA.

Having now fully described the invention, it will be apparent to one of ordinary skill in the art that many changes and modifications can be made thereto without departing from the spirit or scope of the invention as set forth herein.

What is claimed as new and is intended to be secured by Letters Patent of the United States is:

1. A method of separating pyromellitic acid dianhydride from the reaction gas obtained from the gas phase oxidation of 1,2,4,5-tetraalkylbenzene with an oxygen bearing gas in a closed gas circulatory system, comprising:
   (a) desublimating pyromellitic acid dianhydride by contacting the product gas obtained from said gas phase oxidation reaction with a cold, oxygen bearing gas;
   (b) catalytically burning the byproducts in the waste gas obtained from the desublimation step; and
   (c) recirculating a proportionate amount of the byproduct free waste gas to the oxidation reactor for the gas phase oxidation reaction.

2. The method of claim 1, wherein the oxygen bearing gas of the closed gas circulatory system and the oxygen bearing gas used in the desublimation step is a mixture of oxygen and nitrogen and/or carbon dioxide and/or water (steam).

3. The method of claim 2, wherein said oxygen bearing gas is air.

4. The method of claim 1, wherein said oxygen bearing gas in step (a) contains organic compounds which do not disrupt the desublimation of pyromellitic acid dianhydride and which facilitate the catalytic combustion of byproducts in the waste gas.

5. The method of claim 1, wherein a portion of the waste gas obtained from the catalytic combustion of byproducts in said waste gas is recirculated to desublimation step (a) as the cold oxygen bearing gas, thereby forming a second closed gas loop in the system.

6. The method of claim 5, wherein the remaining portion of said waste gas not returned to desublimation step (c) is vented to the atmosphere.

7. The method of claim 1, wherein the ratio of cold oxygen bearing gas added in said desublimation step to the reaction gas which contains pyromellitic acid dianhydride ranges from about 0.4–1.5:1.

8. The method of claim 7, wherein said gas ratio is about 1:1.

* * * * *